United States Patent [19]

Wild

[11] Patent Number: 4,528,369
[45] Date of Patent: Jul. 9, 1985

[54] 20-DIHYDRO-20-DEOXY-23-DE(-MYCINOSYLOXY)TYLOSIN

[75] Inventor: Gene M. Wild, Indianapolis, Ind.

[73] Assignee: Eli Lilly and Company, Indianapolis, Ind.

[21] Appl. No.: 525,064

[22] Filed: Aug. 22, 1983

Related U.S. Application Data

[62] Division of Ser. No. 394,599, Jul. 2, 1982, Pat. No. 4,423,148.

[51] Int. Cl.$^3$ ............ C07H 17/08; C12P 19/62; A61K 31/71
[52] U.S. Cl. .................. 536/7.1; 435/76; 514/30; 536/16.8
[58] Field of Search ........................ 536/7.1

[56] References Cited

U.S. PATENT DOCUMENTS

| | | | |
|---|---|---|---|
| 3,178,341 | 4/1965 | Hamill et al. | 167/65 |
| 3,459,853 | 8/1969 | Gorman et al. | 424/121 |
| 4,299,953 | 11/1981 | Hamill et al. | 536/7.1 |
| 4,304,856 | 12/1981 | Baltz et al. | 435/76 |
| 4,321,361 | 3/1982 | Baltz et al. | 536/17 R |
| 4,321,362 | 3/1982 | Baltz et al. | 536/17 R |
| 4,345,069 | 8/1982 | Sakakibara et al. | 536/7.1 |
| 4,419,508 | 12/1983 | Baltz et al. | 536/7.1 |

FOREIGN PATENT DOCUMENTS 0033433 8/1981 European Pat. Off.
2058765 4/1981 United Kingdom.

OTHER PUBLICATIONS

Hackh's, "Chemical Dictionary", 4th Ed., p. 312.
H. Matsubara et al., "Chemical Transformation of Tylosin, a 16-Membered Macrolide, and its Structure-Activity Relationship", Chem. Pharm. Bull., 30, (1), 97-110, (1982).
A. Nagel et al., "Selective Cleavage of the Mycinose Sugar from the Macrolide Antibiotic Tylosin: A Unique Glycosidic Scission", J. Org. Chem., 44, (12), 2050-2052, (1979).
A. Kinumaki et al., "Macrolide Antibiotics M-4365 Produced by Micromonospora II. Chemical Studies," J. Antibiotic, 30, (6), 450-454, (1977).

Primary Examiner—Johnnie R. Brown
Attorney, Agent, or Firm—Nancy J. Harrison; Arthur R. Whale

[57] ABSTRACT

20-Dihydro-20-deoxy-23-de(mycinosyloxy)tylosin (20-deoxo-DMOT), specified 2'-acyl ester derivatives, and their acid addition salts are useful intermediates and antibacterial agents. Methods of preparing 20-deoxo-DMOT and 5-O-mycaminosyltylactone by fermentation of Streptomyces fradiae ATCC 31733 are included.

11 Claims, 1 Drawing Figure

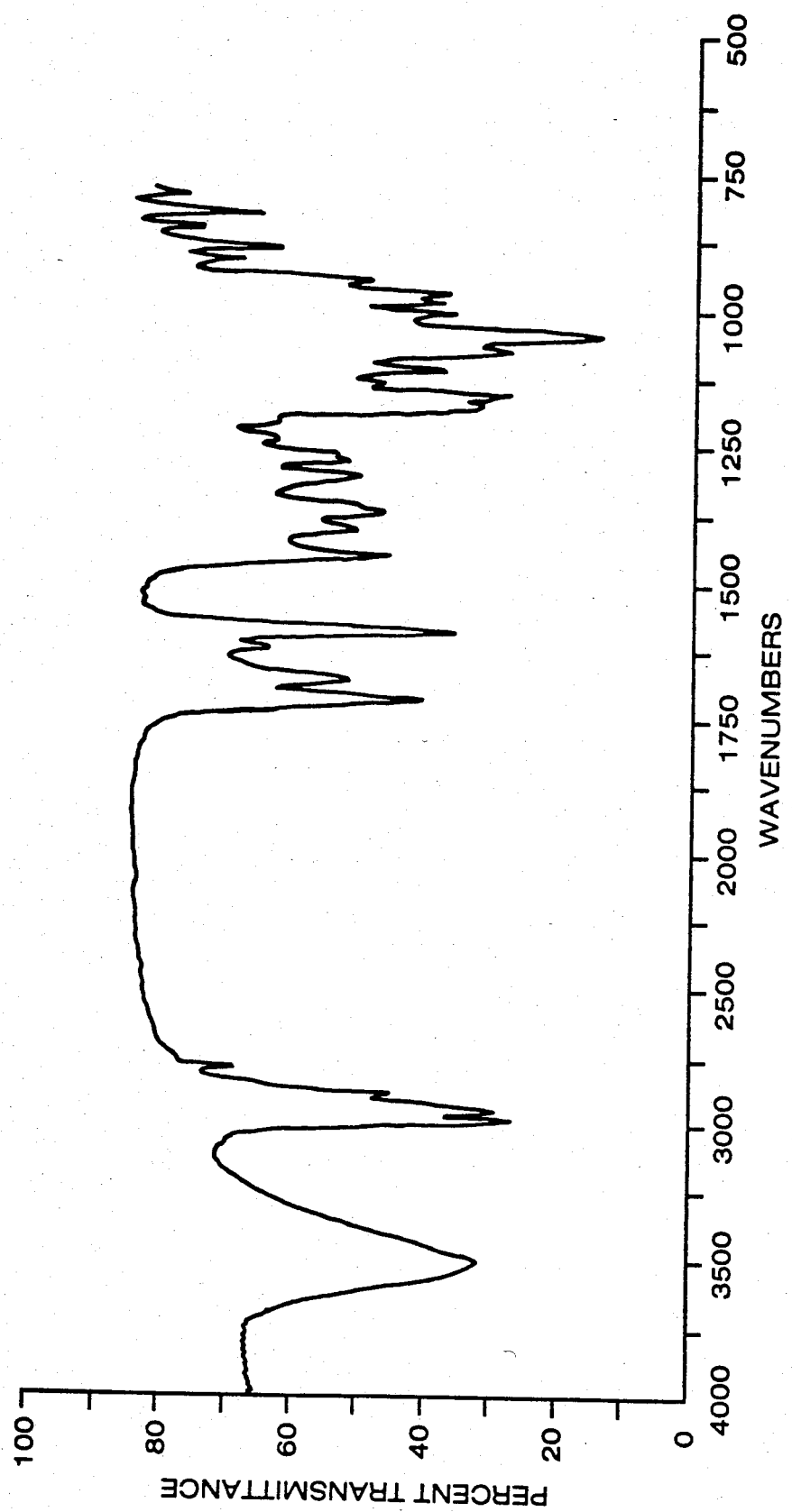

20-DIHYDRO-20-DEOXY-23-DE(MYCINOSYLOX-Y)TYLOSIN

This application is a division of application Ser. No. 394,599, filed 7/2/82, now U.S. Pat. No. 4,423,148, issued 12/30/83.

SUMMARY OF THE INVENTION

This invention relates to 20-dihydro-20-deoxy-23-de(-mycinosyloxy)tylosin and to its 2'-ester derivatives, which are new macrolide antibiotics. 20-Dihydro-20-deoxy-23-de(mycinosyloxy)tylosin, which will be called 20-deoxo-DMOT for convenience herein, and its 2' esters have structure 1:

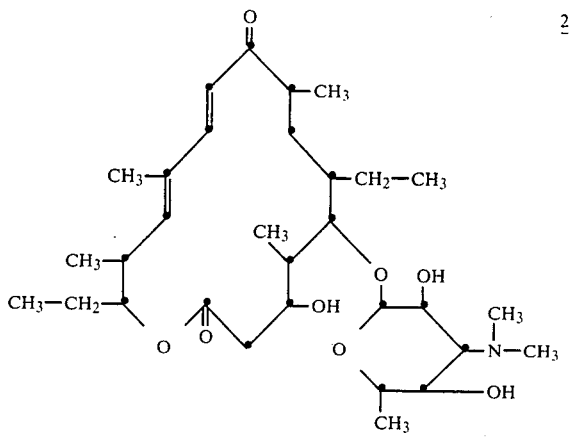

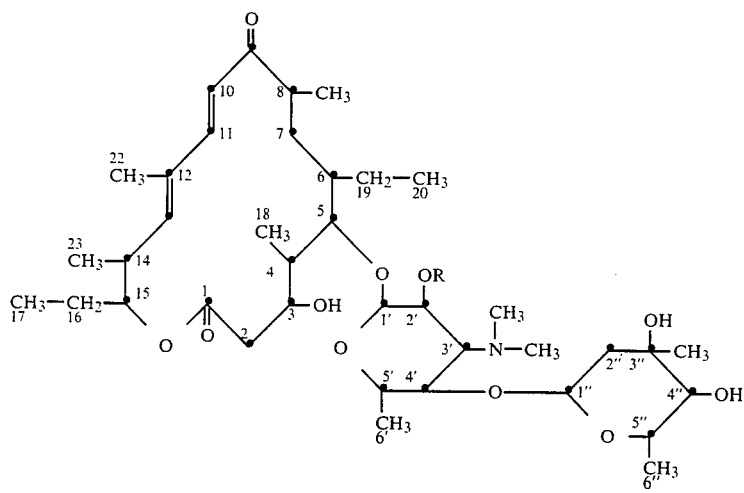

wherein R is hydrogen, $C_1$–$C_5$-alkanoyl, halo-substituted $C_1$–$C_5$-alkanoyl or benzoyl, phenylacetyl or phenylpropionyl, each of which may be substituted on the phenyl portion of the moiety by from one to five halo or methyl groups or by from one to two methoxyl, nitro or hydroxyl groups. The acid addition salts of the formula 1 compounds are also part of this invention.

This invention also provides a new process for the preparation of 5-O-mycaminosyltylactone, which will be called mycaminosyltylactone for convenience herein, by mild acid hydrolysis of 20-deoxo-DMOT. Mycaminosyltylactone has structure 2:

20-Deoxo-DMOT is a useful intermediate in the preparation of antibacterial agents and fermentation intermediates such as mycaminosyltylactone. The products are active against gram-positive microorganisms and Mycoplasma species.

This invention further relates to a method of producing 20-deoxo DMOT or mycaminosyltylactone by culturing a strain of Streptomyces fradiae under submerged aerobic fermentation conditions until a substantial level of antibiotic activity is produced. 20-Deoxo-DMOT and mycaminosyltylactone can be extracted from basified broth filtrate with polar organic solvents, and can be further purified by extraction, chromatographic and-/or crystallization techniques.

DESCRIPTION OF THE DRAWING

The infrared absorption spectrum of 20-deoxo-DMOT (free base) in chloroform is presented in the accompanying drawing.

DETAILED DESCRIPTION

This invention relates to new antibiotics. In particular, this invention relates to new macrolide antibiotics which have formula 1:

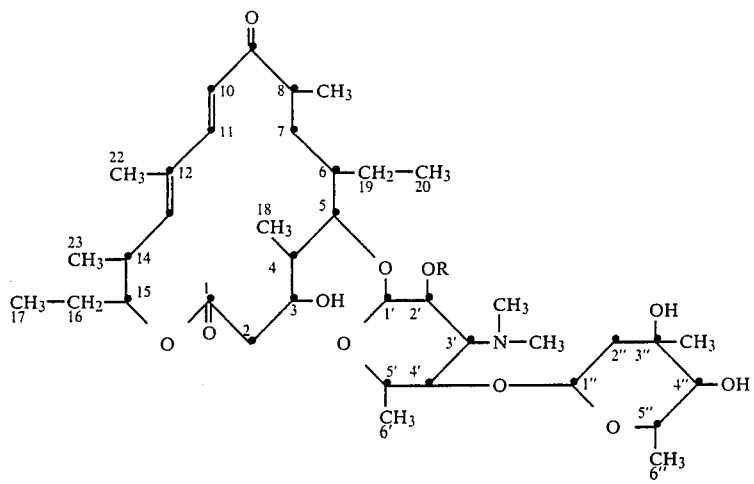

1 wherein R is hydrogen, $C_1$-$C_5$-alkanoyl, halo-substituted $C_1$-$C_5$-alkanoyl or benzoyl, phenylacetyl or phenylpropionyl, each of which may be substituted on the phenyl portion of the moiety by from one to five halo or methyl groups or by from one to two methoxyl, nitro or hydroxyl groups; and to their acid addition salts. The compound of formula 1 wherein R is hydrogen is 20-deoxo-DMOT. This invention also relates to a process for preparing 20-deoxo-DMOT and mycaminosyltylactone by submerged aerobic fermentation of a strain of *Streptomyces fradiae.*

New, improved antibiotics are continually in demand. Better antibiotics are needed for treating human diseases, and improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

20-Deoxo-DMOT is a new member of a group of 16-membered macrolide antibiotics. Members of this group include tylosin (see U.S. Pat. No. 3,178,341), 5-O-mycaminosyltylonolide (see M. Gorman et al., U.S. Pat. No. 3,459,853), antibiotic M-4365G$_2$ [Japanese examined patent 6037-351 (Derwent abstract 86252X)], 23-demycinosyltylosin (DMT) (Baltz et al., U.S. Pat. No. 4,321,361), and 23-de(mycinosyloxy)tylosin (DMOT) (Baltz et al., U.S. Pat. No. 4,321,362).

20-Deoxo-DMOT is a newly discovered factor produced by *Streptomyces fradiae* ATCC 31733. Major factors produced by this culture are 20-dihydro-20-deoxy-23-demycinosyltylosin (DH-DO-DMT) and 20-dihydro-20-deoxy-5-O-mycaminosyltylonolide (DH-DO-OMT), as reported by Baltz et al. in U.S. Pat. No. 4,304,856. Another newly discovered factor produced by this culture is mycaminosyltylactone. This compound was obtained by chemical synthesis by H. Matsubara, et al., *Chem. Pharm. Bull.* 30, 97–100 (1982). DH-DO-DMT and DH-DO-OMT are major factors produced by *S. fradiae* ATCC 31733, and 20-deoxo-DMOT and mycaminosyltylactone are minor factors produced by this culture.

Thus, this invention provides 20-deoxo-DMOT and a method for making both 20-deoxo-DMOT and mycaminosyltylactone by culture of *Streptomyces fradiae* 31733.

The following paragraphs describe the properties of 20-deoxo-DMOT.

20-DEOXO-DMOT

20-Deoxo-DMOT is the compound of formula 1 wherein R is hydrogen. Although no stereochemical assignments are indicated, the stereochemistry of the antibiotic is identical to that of tylosin. The neutral sugar is mycarose, and the amino-sugar is mycaminose.

20-Deoxo-DMOT is a white solid with the following approximate percentage elemental composition: carbon, 64%; hydrogen, 9%; nitrogen, 2%; oxygen, 25%. 20-Deoxo-DMOT has an empirical formula of $C_{38}H_{65}NO_{11}$ and a molecular weight of about 711 (711 as determined by field-desorption mass spectrometry).

The infrared absorption spectrum of 20-deoxo-DMOT free base in chloroform is shown in the accompanying drawing. Observable absorption maxima occur at the following frequencies ($cm^{-1}$): 3482 (broad, strong), 3477 (strong), 2971 (strong), 2877 (medium to strong), 2785 (weak), 1717 (medium to strong), 1685 (medium), 1630 (weak), 1595 (medium to strong), 1457 (medium), 1410 (medium to weak), 1380 (medium to weak), 1314 (medium to weak), 1285 (medium to weak), 1275 (shoulder), 1246 (weak), 1218 (very weak), 1181 (medium to strong), 1162 (medium to strong), 1143 (very weak), 1119 (medium), 1081 (medium), 1052 (very strong), 1017 (medium to weak), 996 (medium to weak), 981 (weak), 961 (weak), 927 (weak), 904 (weak), 870 (weak), 843 (medium to weak) and 807 (weak).

The ultraviolet absorption spectrum of 20-deoxo-DMOT in 95% neutral ethanol exhibits an absorption maximum at 281 nm ($\epsilon$26,431).

20-Deoxo-DMOT (free base) has the following specific rotation: $[\alpha]_D^{25} - 55.5°$ (c 0.5, $CH_3OH$).

20-Deoxo-DMOT as a free base is slightly soluble in water and is soluble in most polar organic solvents such as acetone, methanol, ethanol, chloroform, dimethylformamide and dimethyl sulfoxide. Acid addition salts of 20-deoxo-DMOT are more soluble in water than is the free base.

20-Deoxo-DMOT and mycaminosyltylactone can be distinguished from each other and from co-produced factors by thin-layer chromatography (TLC). The approximate Rf values of 20-deoxo-DMOT and mycaminosyltylactone in one useful TLC system are summarized in Table I. Ultraviolet absorption was used for detection.

TABLE I

Thin-Layer Chromatography Data[a,b]

| Compound | Rf Value |
|---|---|
| 20-Deoxo-DMOT | 0.84 |
| Mycaminosyltylactone | 0.62 |
| DH-DO-OMT | 0.39 |
| DH-DO-DMT | 0.50 |

[a]Medium: E. Merck, Darmstadt - Silica Gel 60
[b]Solvent: ethyl acetate:diethylamine (95:5)

PREPARATION OF MYCAMINOSYLTYLACTONE FROM DEOXO-DMOT

This invention also relates to a method of preparing mycaminosyltylactone by mild acid hydrolysis of 20-deoxo-DMOT. Mild acid hydrolysis conditions are known in the art. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating 20-deoxo-DMOT with a mild acid solution for a time sufficient to effect removal of the mycarosyl group to give mycaminosyltylactone.

Alternatively, and sometimes preferably, mycaminosyltylactone can be prepared by treating 20-deoxo-DMOT in the fermentation broth in which it is produced, using mild acidic conditions as described above for a time sufficient to convert the 20-deoxo-DMOT to mycaminosyltylactone, which can be isolated from the fermentation broth using techniques herein described.

ESTER DERIVATIVES

20-Deoxo-DMOT can be esterified on the 2'-hydroxyl group to give acyl ester derivatives by treatment with acylating agents using methods known in the art. Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide. Once formed, the acyl derivatives can be separated and purified by known techniques.

Esterification of the 2'-group of 20-deoxo-DMOT is most facile. Thus, esterification of 20-deoxo-DMOT gives 2'-monoester derivatives by selective esterification techniques generally known in the art, such as, for example, treatment of the antibiotic with a stoichiometric quantity (or a slight excess) of an acylating agent, such as an acyl anhydride, at about room temperature for from about 1 to about 24 hours until esterification is substantially complete. These derivatives can be isolated from the reaction mixture by standard procedures such as extraction, chromatography and crystallization. The 2'-monoesters of mycaminosyltylactone can be prepared by hydrolyzing the corresponding 2'-monoester of 20-deoxo-DMOT, using mildly acidic conditions as described above.

Representative suitable esters include those derived from acids such as acetic, chloroacetic, propionic, butyric, isovaleric, benzoic, phenylacetic, and phenylpropionic acids.

SALTS

20-Deoxo-DMOT and its ester derivatives form acid addition salts which are also part of this invention. Such salts are useful, for example, for separating and purifying 20-deoxo-DMOT and its acyl derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and the like acids.

PREPARATION OF 20-DEOXO-DMOT AND MYCAMINOSYLTYLACTONE BY S. FRADIAE

20-Deoxo-DMOT and mycaminosyltylactone are prepared by culturing a strain of Streptomyces fradiae, such as S. fradiae ATCC 31733, which produces these compounds under submerged aerobic conditions in a suitable culture medium until substantial antibiotic activity is produced. The culture medium used to grow Streptomyces fradiae ATCC 31733 can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal, and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of 20-deoxo-DMOT or mycaminosyltylactone, submerged aerobic fermentation in tanks is preferred. Small quantities of these compounds may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

S. fradiae ATCC 31733 can be grown at temperatures between about 10° and about 40° C. Optimum antibiotic production appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Antibiotic production can be followed during the fermentation by testing samples of the broth against organisms known to be sensitive to these antibiotics. One useful assay organism is Staphylococcus aureus ATCC 9144. The bioassay is conveniently performed by an automated turbidometric method. In addition, antibiotic production can be readily monitored by high-performance liquid chromatography with UV detection.

Following its production under submerged aerobic fermentation conditions, 20-deoxo-DMOT or mycaminosyltylactone can be recovered from the fermentation medium by methods used in the art. In the recovery process the fermentation broth is first filtered to remove mycelia. The filtered broth can then be further purified to give the desired antibiotic. A variety of techniques may be used in this purification. A preferred technique for purification of the filtered broth involves adjusting the broth to about pH 9; extracting the broth with a suitable solvent such as ethyl acetate, amyl acetate, or methyl isobutyl ketone; extracting the organic phase with an aqueous acidic solution; adjusting the pH of the aqueous extract; and again extracting with a suitable solvent such as dichloromethane. Further purification involves the use of extraction, chromatographic and/or precipitation techniques.

The microorganism which produces 20-deoxo-DMOT and mycaminosyltylactone was obtained by chemical mutagenesis of a Streptomyces fradiae strain which produced tylosin. The microorganism produces only minimal amounts of tylosin, but produces DH-DO-DMT and DH-DO-OMT (in approximately equal amounts) as major components and 20-deoxo-DMOT and mycaminosyltylactone as minor components. This Streptomyces fradiae culture has been deposited and made part of the stock culture collection of The American Type Culture Collection, 12301 Parklawn Drive, Rockville, Md., 20852, from which it is available to the public under the accession number ATCC 31733.

As is the case with other organisms, the characteristics of Streptomyces fradiae ATCC 31733 are subject to variation. For example, artificial variants and mutants of the ATCC 31733 strain may be obtained by treatment with various known physical and chemical mutagens, such as ultraviolet rays, X-rays, gamma rays, and N-methyl-N'-nitro-N-nitrosoguanidine. All natural and artificial variants, mutants and recombinants of Streptomyces fradiae ATCC 31733 which retain the characteristic of production of 20-deoxo-DMOT and/or mycaminosyltylactone may be used in this invention.

20-Deoxo-DMOT and mycaminosyltylactone inhibit the growth of pathogenic bacteria, especially gram-positive bacteria and Mycoplasma species. Tables II and III summarize the minimal inhibitory concentrations (MIC) at which 20-deoxo-DMOT and mycaminosyltylactone (as free bases) inhibit certain organisms. The MIC's in Table II were determined by standard agar-dilution assays. The MIC's in Table III were obtained using a conventional broth-dilution microtiter test.

TABLE II

In Vitro Activity of 20-Deoxo-DMOT and Mycaminosyltylactone

| Organism | MIC ($\mu$g/ml) 20-De-oxo-DMOT | Mycaminosyl-tylactone |
|---|---|---|
| Staphylococcus aureus NRRL B313 | 128 | 16 |
| Staphylococcus aureus V41 | 64 | 16 |
| Staphylococcus aureus X400 | 128 | 32 |
| Staphylococcus aureus S13E | 64 | 8 |
| Staphylococcus epidermidis EPI1 | 64 | 8 |
| Staphylococcus epidermidis EPI2 | 64 | 16 |
| Streptococcus pyogenes C203 | 128 | 32 |
| Streptococcus pneumoniae Park 1 | 64 | 4 |
| Streptococcus faecium ATCC 9790 | >128 | 32 |
| Streptococcus sp. group D 9960 | >128 | 32 |
| Haemophilus influenzae C.L. | >128 | 16 |
| Haemophilus influenzae 76 | >128 | 16 |
| Shigella sonnei N9 | >128 | >128 |
| Escherichia coli N10 | >128 | >128 |
| Escherichia coli EC14 | >128 | >128 |
| Escherichia coli TEM | >128 | >128 |
| Klebsiella pneumoniae X26 | >128 | 8 |
| Klebsiella pneumoniae KAE | >128 | >128 |

TABLE III

In Vitro Activity of 20-Deoxo-DMOT and Mycaminosyltylactone

| Organism | MIC ($\mu$g/ml) 20-Deoxo-DMOT | Mycaminosyl-tylactone |
|---|---|---|
| Pasteurella multocida 17E[a] | >50 | 12.5 |
| Pasteurella multocida 60A[b] | >50 | 12.5 |
| Pasteurella hemolytica 22C | >50 | 25 |
| Mycoplasma gallisepticum | >50 | 1.56 |
| Mycoplasma synoviae | 50 | 12.5 |
| Mycoplasma hyorhinis | 50 | 50 |

[a]Bovine isolate
[b]Avian isolate

Although 20-deoxo-DMOT and its derivatives have some antibacterial activity, these compounds are best used as intermediates to the corresponding mycaminosyltylactone compounds.

Mycaminosyltylactone, its acyl ester derivatives and their acid addition salts can also be used as surface disinfectants. Solutions containing as little as 0.01% by weight are useful for disinfecting purposes. Such solutions, preferably also containing a detergent or other cleansing agent, are useful for disinfecting objects and surfaces where maintenance of sterile conditions is important.

In order to illustrate more fully the operation of this invention, the following examples are provided:

EXAMPLE 1

A. Shake-flask Fermentation of 20-Deoxo-DMOT and Mycaminosyltylactone

A lyphilized pellet of Streptomyces fradiae ATCC 31733 is dispersed in 1-2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |

-continued

| Ingredient | Amount (%) |
|---|---|
| Soybean grits | 0.5 |
| CaCO₃ | 0.3 |
| Soybean oil (crude) | 0.45 |
| Deionized water | 97.25 |

Alternatively, a vegetative culture of *S. fradiae* ATCC 31733 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of 20-Deoxo-DMOT and Mycaminosyltylactone

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
|---|---|
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
|---|---|
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |

| Ingredient | Amount (%) |
|---|---|
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

EXAMPLE 2

Isolation of 20-Deoxo-DMOT and Mycaminosyltylactone

Whole broth (925 L), prepared in a manner similar to that described in Example 1, section B, is filtered using a filtration aid. The mycelial cake is washed with water; and the filtrate and wash solution (886 L) is adjusted to pH 9.3 with 25% sodium hydroxide. The resulting solution is extracted twice with ethyl acetate (371 L and 185 L). The ethyl acetate extracts are combined and extracted twice with a dilute phosphoric acid solution (125 L of water adjusted to pH 4.1 by the addition of 28% H$_3$PO$_4$). The combined aqueous extracts (300 L), adjusted to pH 8.5–9.0 with 10% sodium hydroxide, are extracted twice with dichloromethane (100 L each). The dichloromethane extracts are dried to give 1.02 kg of solid material.

Three portions of this material (50 g each) were dissolved in ethyl acetate and treated, using several six-stage countercurrent distribution procedures, with ethyl acetate or ethyl acetate-heptane mixtures as the solvent phase and 0.5M phosphate buffer at pH's of 4.0 to 5.5 to give 4.5 g of purified product.

This product was further purified by silica-gel chromatography (E. Merck 7734), developing with solvents containing 50–80 parts heptane, 20–50 parts ethyl acetate and 5 parts diethylamine to give 3 g of material containing only 20-deoxo-DMOT and mycaminosyltylactone.

This material was chromatographed on a silica-gel column (75 g), prepared and eluted with methanol, to give 1.48 g of 20-deoxo-DMOT and 80 mg of mycaminosyltylactone.

EXAMPLE 3

Preparation of Mycaminosyltylactone from 20-Deoxo-DMOT

20-Deoxo-DMOT, prepared as described in Example 2, is dissolved in a dilute hydrochloric acid solution (HCl added to the water solution until the pH of the solution is 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is dried and evaporated under vacuum to give mycaminosyltylactone.

EXAMPLE 4

Alternative Preparation of Mycaminosyltylactone

Mycaminosyltylactone is prepared from 20-deoxo-DMOT by treating the 20-deoxo-DMOT in the fermentation broth in which it is produced with mild acid as described in Example 3. Isolation of the mycaminosyltylactone is accomplished by a procedure similar to that described in Example 2.

EXAMPLE 5

2'-O-Propionyl-20-Deoxo-DMOT

20-Deoxo-DMOT is dissolved in acetone and treated with 1.2 equivalents of propionic anhydride at room temperature for about six hours to give 2'-O-propionyl-20-deoxo-DMOT.

EXAMPLES 6-9

2'-O-Isovaleryl-20-deoxo-DMOT, prepared according to the procedure of Example 5, but using isovaleric anhydride.

2'-O-Benzoyl-20-deoxo-DMOT, prepared according to the procedure of Example 5 but using benzoic anhydride.

2'-O-(n-Butyryl)-20-deoxo-DMOT, prepared according to the procedure of Example 5, but using n-butyric anhydride.

2'-O-Acetyl-20-deoxo-DMOT, prepared according to the procedure of Example 5 but using acetic anhydride.

EXAMPLE 10

2'-O-Propionyl-mycaminosyltylactone, prepared by hydrolyzing 2'-O-propionyl-deoxo-DMOT of Example 5, using the procedure of Example 3.

EXAMPLES 11-14

2'-O-Isovaleryl-mycaminosyltylactone, prepared according to the procedure of Example 10, but using 2'-O-isovaleryl-20-deoxo-DMOT.

2'-O-Benzoyl-mycaminosyltylactone, prepared according to the procedure of Example 10, but using 2'-O-benzoyl-20-deoxo-DMOT. 2'-O-(n-Butyryl)-mycaminosyltylactone, prepared according to the procedure of Example 10, but using 2'-O-(n-butyryl)-20-deoxo-DMOT.

2'-O-Acetyl-mycaminosyltylactone, prepared according to the procedure of Example 10, but using 2'-O-acetyl-20-deoxo-DMOT.

I claim:
1. A compound of the formula

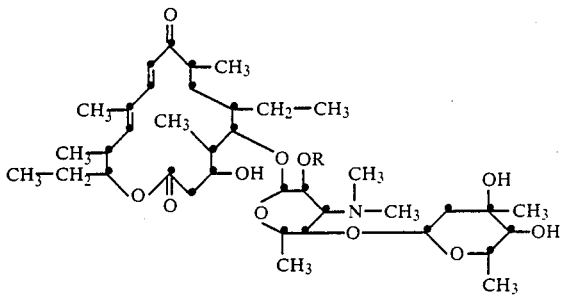

wherein R is hydrogen, $C_1$–$C_5$-alkanoyl, halo-substituted $C_1$–$C_5$-alkanoyl, benzoyl, phenylacetyl or phenylpropionyl, or benzoyl, phenylacetyl or phenylpropionyl substituted on the phenyl portion of the moiety by from one to five halo or methyl groups or by from one to two methoxyl, nitro or hydroxyl groups; and its acid addition salts.

2. The compound of claim 1 wherein R is hydrogen.

3. A compound of claim 1 wherein R is $C_1$–$C_5$ alkanoyl or halo-substituted $C_1$–$C_5$ alkanoyl.

4. A compound of claim 1 wherein R is benzyl, phenylacetyl, or phenylpropionyl, or benzoyl, phenylacetyl or phenylpropionyl substituted on the phenyl portion of the moiety by from one to five halo or methyl groups or by from one to two methoxyl, nitro or hydroxyl groups.

5. A compound of claim 1 which is an acid addition salt.

6. A compound of claim 5 which is the tartrate salt.

7. A compound of claim 5 which is the hydrochloride salt.

8. A compound of claim 5 which is the phosphate salt.

9. The process for preparing 5-O-mycaminosyltylactone which comprises treating 20-dihydro-20-deoxy-23-de(mycinosyloxy)tylosin with a mild acid solution until 5-O-mycaminosyltylactone is formed.

10. The method of claim 9 wherein the 20-dihydro-20-deoxy-23-de(mycinosyloxy)tylosin is treated in the fermentation broth in which it is produced.

11. The process for preparing the 2'-monoesters of 5-O-mycaminosyltylactone, which comprises treating the corresponding 2'-monoester of 20-dihydro-20 -deoxy-23-de(mycinosyloxy)tylosin with a mild acid solution until the 2'-monoester of 5-O-mycaminosyltylactone is formed.

* * * * *

UNITED STATES PATENT AND TRADEMARK OFFICE
CERTIFICATE OF CORRECTION

PATENT NO. : 4,528,369
DATED : July 9, 1985
INVENTOR(S) : Gene M. Wild

It is certified that error appears in the above—identified patent and that said Letters Patent is hereby corrected as shown below:

Column 12, line 25, "R is benzyl" should read -- R is benzoyl --.

Signed and Sealed this

Twenty-seventh Day of May 1986

[SEAL]

Attest:

DONALD J. QUIGG

Attesting Officer

Commissioner of Patents and Trademarks